(12) United States Patent
Tang et al.

(10) Patent No.: US 10,198,812 B2
(45) Date of Patent: Feb. 5, 2019

(54) DATA FIDELITY WEIGHT DESIGN FOR ITERATIVE RECONSTRUCTION

(71) Applicant: Toshiba Medical Systems Corporation, Otawara-shi (JP)

(72) Inventors: Qiulin Tang, Buffalo Grove, IL (US); Jian Zhou, Buffalo Grove, IL (US); Zhou Yu, Wilmette, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 59 days.

(21) Appl. No.: 15/282,437

(22) Filed: Sep. 30, 2016

(65) Prior Publication Data

US 2018/0096476 A1 Apr. 5, 2018

(51) Int. Cl.
| | |
|---|---|
| G06K 9/00 | (2006.01) |
| G06T 7/00 | (2017.01) |
| H04N 19/426 | (2014.01) |
| A61B 6/03 | (2006.01) |

(Continued)

(52) U.S. Cl.
CPC .......... G06T 7/0012 (2013.01); *A61B 6/032* (2013.01); *A61B 6/035* (2013.01); *A61B 6/5205* (2013.01); *A61B 6/5258* (2013.01); *G06T 11/005* (2013.01); *G06T 11/008* (2013.01); *H04N 19/426* (2014.11); *G06T 2207/10081* (2013.01); *G06T 2207/10116* (2013.01); *G06T 2207/30004* (2013.01); *G06T 2211/424* (2013.01)

(58) Field of Classification Search
None
See application file for complete search history.

(56) References Cited

U.S. PATENT DOCUMENTS

| | | | |
|---|---|---|---|
| 9,261,467 B2 * | 2/2016 | Thibault | G01N 23/046 |
| 2012/0294414 A1 * | 11/2012 | Koehler | A61B 6/032 |
| | | | 378/16 |
| 2013/0101190 A1 | 4/2013 | Shi et al. | |

(Continued)

OTHER PUBLICATIONS

Dieter Hahnl, Pierre Thibault2, Andreas Fehringerl, Martin Bech3, Thomas Koehler4,5, Franz Pfeiffer & Peter B. Noël, Statistical iterative reconstruction algorithm for X-ray phase-contrast CT, "Scientific Reports," received: Oct. 20, 2014, accepted: Apr. 14, 2015, Published: Jun. 12, 2015.

(Continued)

*Primary Examiner* — Soo Jin Park
(74) *Attorney, Agent, or Firm* — Oblon, McClelland, Maier & Neustadt, L.L.P.

(57) ABSTRACT

A method and apparatus is provided to determine a reconstructed image from computed tomography projection data using iterative reconstruction with an objective function that includes modified weights. The modified weights can include, among other weight values, redundancy weights and statistical weights, which are modified to compress low-frequency components. Additionally, high-frequency components of the statistical weights can be compressed, amplified, or maintained at their current magnitude. The high-frequency components can be subject to a threshold-and-invert step, substituting an inverted value for each high-frequency component above a predefined threshold. Using the modified weights, the reconstructed image can be determined using penalized weighted least squares to minimize the objective function.

20 Claims, 19 Drawing Sheets

(51) Int. Cl.
*A61B 6/00* (2006.01)
*G06T 11/00* (2006.01)

(56) References Cited

U.S. PATENT DOCUMENTS

2013/0121553 A1   5/2013   Thibault et al.
2014/0086466 A1   3/2014   Schwarz et al.
2014/0369463 A1   12/2014  Thibault et al.
2015/0117732 A1   4/2015   Zamyatin et al.

OTHER PUBLICATIONS

Jana Hwan Cho and Jeffrey A. Fessler, "Regularization Designs for Uniform Spatial Resolution and Noise Properties in Statistical Image Reconstruction for 3D X-ray CT," IEEE Trans Med Imaging. Feb. 2015; 34(2): 673-689.
Zhiqian Chang, Ruoqiao Zhang, Jean-Baptiste Thibault, Debashish Pal, Lin Fu, Ken Sauer, Charles Bouman, "Adaptive Regularization for Uniform Noise Covariance in Iterative 3D CT," Proceedings of Fully3d 2015.

\* cited by examiner

Streaks

Artifacts from greater weighting of tangential rays

DATA FIDELITY WEIGHT DESIGN FOR ITERATIVE RECONSTRUCTION

FIELD

This disclosure relates to image reconstruction using iterative reconstruction, and, more particularly, to iterative reconstruction using penalized weighted least squares with an objective function that uses modified data-fidelity weights.

BACKGROUND

Computed tomography (CT) systems and methods are widely used, particularly for medical imaging and diagnosis. CT systems generally create images of one or more sectional slices through a subject's body. A radiation source, such as an X-ray source, irradiates the body from one side. At least one detector on the opposite side of the body receives radiation transmitted through the body. The attenuation of the radiation that has passed through the body is measured by processing electrical signals received from the detector.

A CT sinogram indicates attenuation through the body as a function of position along a detector array and as a function of the projection angle between the X-ray source and the detector array for various projection measurements. In a sinogram, the spatial dimensions refer to the position along the array of X-ray detectors. The time/angle dimension refers to the projection angle of X-rays, which changes as a function of time during a CT scan. The attenuation resulting from a portion of the imaged object (e.g., a vertebra) will trace out a sine wave around the vertical axis. Those portions farther from the axis of rotation correspond to sine waves with larger amplitudes, and the phase of the sine waves correspond to the angular positions of objects around the rotation axis. Performing an inverse Radon transform—or any other image reconstruction method—reconstructs an image from the projection data in the sinogram. Two families of reconstructions methods commonly used in clinical applications are filtered-back projection (FBP) and iterative reconstruction (IR).

There has arisen a push to reduce the radiation dose of clinical CT scans to become as low as reasonably achievable. Thus, iterative image reconstruction has been playing a more significant role in CT imaging. Iterative image reconstruction algorithms, as compared with traditional analytical algorithms, are promising in reducing the radiation dose while improving the CT image quality.

In X-ray computed tomography (CT), iterative reconstruction can be used to generate images. While various IR methods exist, one common IR method is optimizing the expression $$\underset{x}{\operatorname{argmin}}\{\|x-y\|_W^2 + \beta U(x)\}$$

to obtain the argument x that minimize the expression. For example, in X-ray CT A is the system matrix that represents X-ray trajectories (i.e., line integrals) along various rays from a source through an object OBJ to an X-ray detector (e.g., the X-ray transform corresponding to projections through the three-dimensional object OBJ onto a two-dimensional projection image y), y represents projection images taken at a series of projection angles and corresponding to the log-transform of the measured X-ray intensity at the X-ray detector, and x represents the reconstructed image of the X-ray attenuation of the object OBJ. The notation $\|g\|_W^2$ signifies a weighted inner product of the form $g^T W g$, wherein W is the weight matrix. For example, the weight matrix W can weigh the pixel values according to their noise statistics (e.g., the signal-to-noise ratio), in which case the weight matrix W is diagonal when the noise of each pixel is statistically independent. The data-fidelity term $\|Ax-y\|_W^2$ is minimized when the forward projection A of the reconstructed image x provides a good approximation to all measured projection images y. In the above expression, U(x) is a regularization term, and β is a regularization parameter that determines the relative contributions of the data-fidelity term and the regularization term.

IR methods augmented with regularization can have several advantages over other reconstruction methods such as filtered back-projection. For example, IR methods augmented with regularization can produce high-quality reconstructions for few-view projection data and in the presence of significant noise. For few-view, limited-angle, and noisy projection scenarios, the application of regularization operators between reconstruction iterations seeks to tune the final and/or intermediate results to some a priori model. For example, minimizing the "total variation" (TV) in conjunction with projection on convex sets (POCS) is also a very popular regularization scheme. The TV-minimization algorithm assumes that the image is predominantly uniform over large regions with sharp transitions at the boundaries of the uniform regions, which is generally true for an image of a discrete number of organs, each with an approximately constant X-ray absorption coefficient (e.g., bone having a first absorption coefficient, the lungs having second coefficient, and the heart having a third coefficient). When the a priori model corresponds well to the image object OBJ, these regularized IR algorithms can produce good image quality even though the reconstruction problem is significantly underdetermined (e.g., few-view scenarios), missing projection angles, or noisy.

If image reconstruction is performed using IR without weighting (e.g., where the weighting matrix W is replaced with an identity matrix), then streak artifacts appear in the reconstructed image. While the streak artifacts can be largely mitigated in IR by using weights that depend, at least in part, on the statistical properties of the data, the weights tend to favor tangential rays passing through the periphery of the subject because these rays are attenuated less, resulting in larger signal-to-noise ratios (SNR) for the tangential rays, which results in a larger weights and a disproportionately large contribution to the reconstructed image due to the tangential rays.

BRIEF DESCRIPTION OF THE DRAWINGS

A more complete understanding of this disclosure is provided by reference to the following detailed description when considered in connection with the accompanying drawings, wherein.

DETAILED DESCRIPTION

Compared with traditional computed tomography (CT) using filtered back-projection (FBP) image reconstruction, fully statistical based iterative reconstruction (IR) can advantageously suppress noise and suppress cone-beam artifacts. However, as discussed above, other artifacts can result from certain rays in given projection angles being given greater weight than others. Generally, increasing the weight given to rays with higher signal magnitudes is advantageous because those rays generally have higher signal-to-noise ratios (SNR) can be trusted more in the reconstruction.

However, rays transmitted through the periphery of a subject, as opposed to rays transmitted through the core, experience weaker attenuation. Thus, a reconstruction favoring high SNR data will disproportionately rely on peripheral rays that tangentially pass through the subject. This over representation of peripheral rays in the reconstructed image generates other artifacts, instead of the streak artifacts. The methods described herein mitigate these other artifacts by modifying the weights W applied in the data fidelity term of an objective function used for iterative reconstruction.

In certain implementations, statistical IR uses a penalized weighted least square (PWLS) approach, which generates a reconstructed image by solving an optimization problem with a cost/objective function $C(\cdot)$, which is given by $$\min_x C(x) = \min_x (Ax - y)^T W (Ax - y) + \beta U(x),$$

wherein A is the system matrix (also referred to as the forward projection operator), x is the image to be reconstructed, y is the measured projection data, U(x) is the regularization function (also referred to as the penalty function), and $\beta$ is the regularization parameter. The weighting is performed by W which is a diagonal weighting matrix. Generally, the weighting matrix can be expressed by using a factored model $$W = W_r W_s W_v$$

wherein $W_r$ is a redundant weight matrix, $W_s$ is a statistical weight matrix, and $W_v$ is another weight matrix. The term on the left-hand side of the objective function is the data fidelity term, and the term on the right-hand side of the objective function is the regularization term.

Figure 1A:
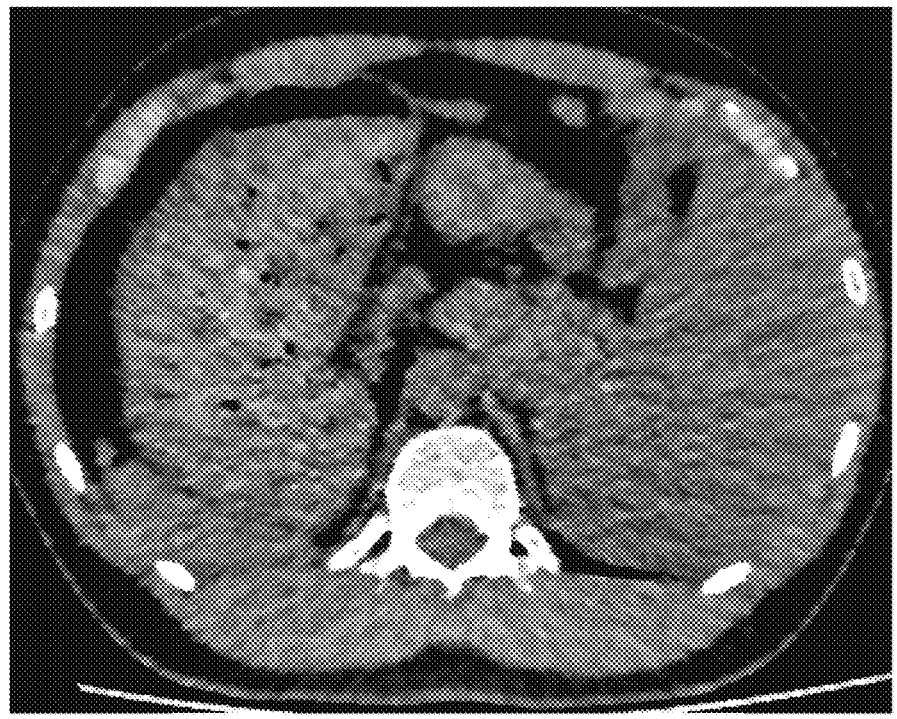
FIG. 1A shows a reconstructed image using iterative reconstruction (IR) without fidelity weighting, according to one implementation.
Figure 3A:
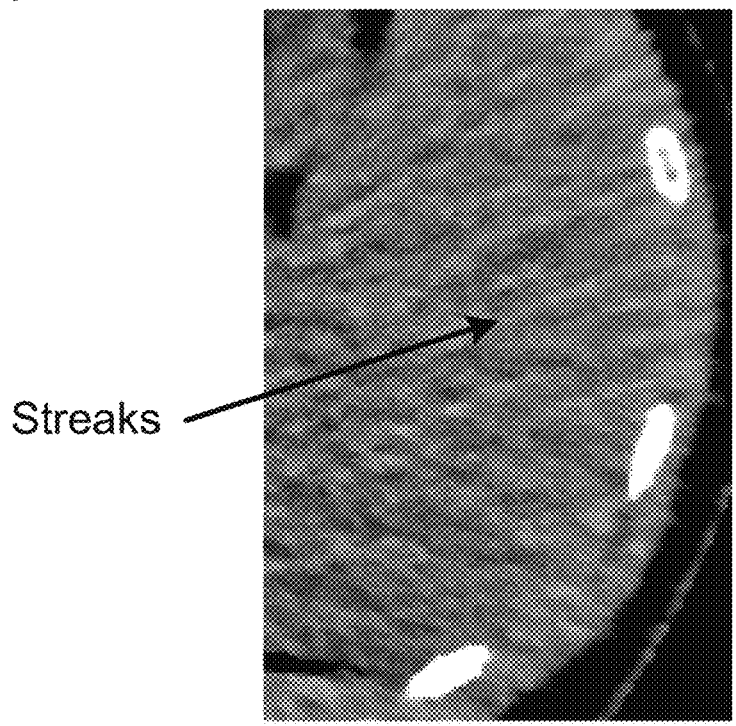
FIG. 3A shows a close up of the reconstructed image from Figure 1A.

Referring now to the drawings, wherein like reference numerals designate identical or corresponding parts throughout the several views, FIG. 1A shows a reconstructed image using an iterative reconstruction (IR) method without data-fidelity weighting. In this image, streaks can be observed radiating predominantly from the center outward, especially in those regions of the image shadowed by the high absorption of the vertebra. FIG. 3A shows a close up of the reconstructed image in FIG. 1A. This close up provides a better view of the streak artifacts.

Figure 1B:
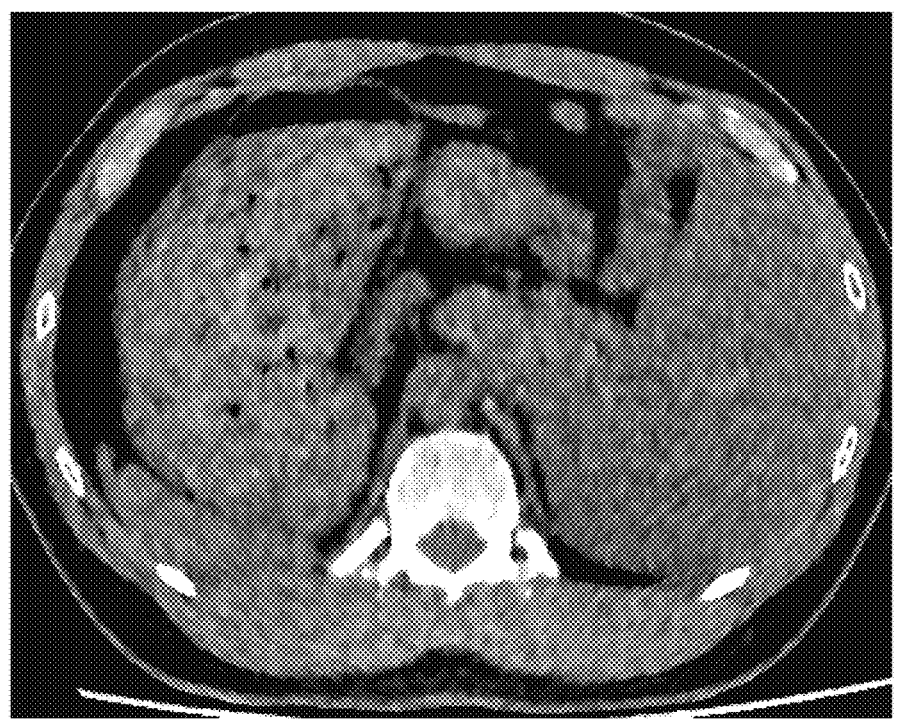
FIG. 1B shows a reconstructed image using IR with fidelity weighting, according to one implementation.
Figure 3B:
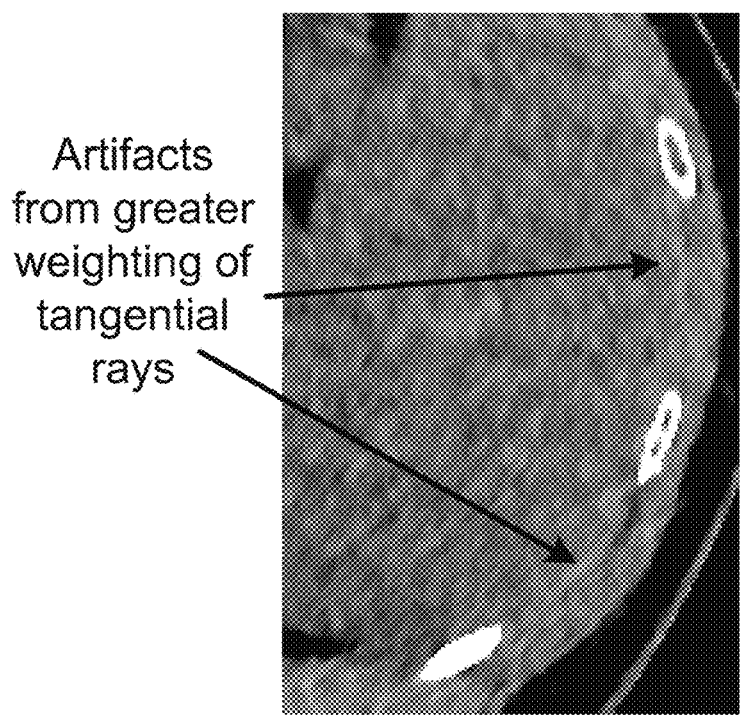
FIG. 3B shows a close up of the reconstructed image from FIG. 1B.

FIG. 1B shows a reconstructed image using an IR method with data-fidelity weighting that incorporates the statistical reliability of the various rays (e.g., using the SNR). In this image, the streak artifacts have been mitigated, but other artifacts can be observed extending conformally a short distance inside the peripheral surface of the subject. FIG. 3B shows a close up of the reconstructed image in FIG. 1B. This close up provides a better view of the tangent-ray artifacts (also referred to as anisotropic and peripheral artifacts). These artifacts result from a disproportionate representation of the tangential rays in the reconstructed image.

Figure 2:
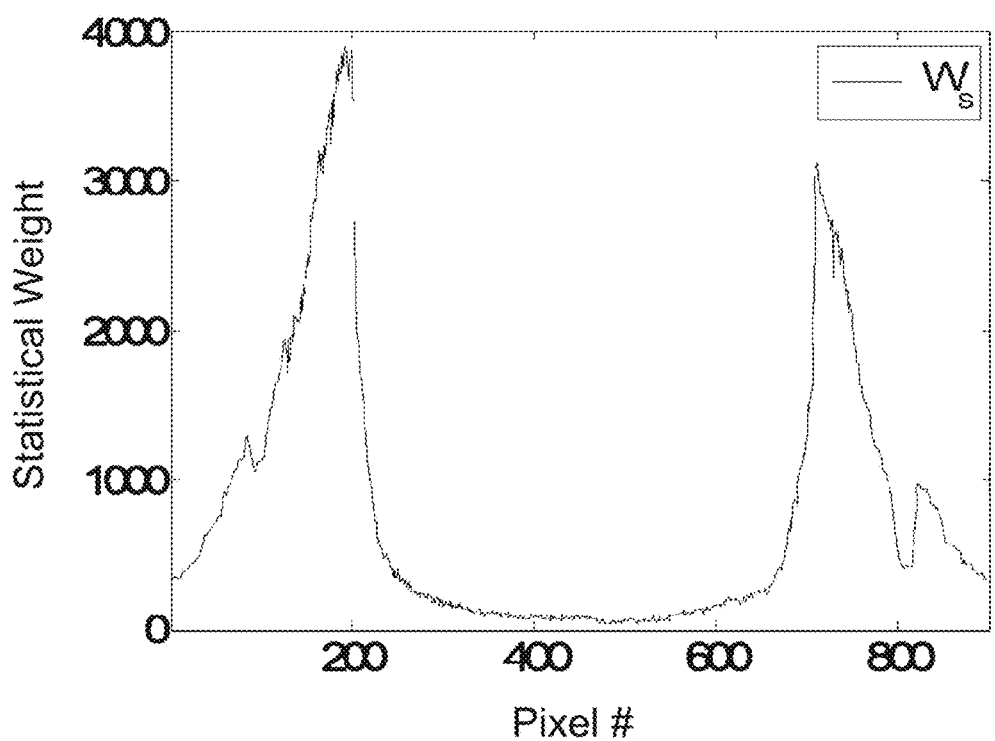
FIG. 2 shows a plot of statistical weights as a function of pixel number, according to one implementation.

FIG. 2 shows a plot of weighting values based on the data-fidelity/statistical properties of the projection data as a function of pixel number plotted across the horizontal axis. Those rays detected nearest the center of the detector array also pass through the core of the subject and experience the greatest attenuation. Thus, the signals for rays passing through the core are lower than for tangential rays near pixel 200 and pixel 700 that pass through peripheral sections of the subject, and the SNR for core rays are correspondingly lower. At the two extreme ends of the detector array, the wings of the X-ray beam decrease in intensity, resulting in a lower SNR, even without passing through the subject. However, these extreme pixel values do not play a significant role in the reconstruction of the image. Thus, as shown in FIG. 2, the tangential/peripheral rays are weighted much higher than the core rays, and, therefore, the pixel values for the tangential/peripheral rays are disproportionately represented in the reconstructed image, resulting in the artifacts seen in FIGS. 1B and 3B. Accordingly, although statistical based IR can suppress artifacts, statistical-based IR can result in other artifacts due to anisotropic resolution and anisotropic noise correlation structure, especially near the periphery of the subject.

Figure 4:
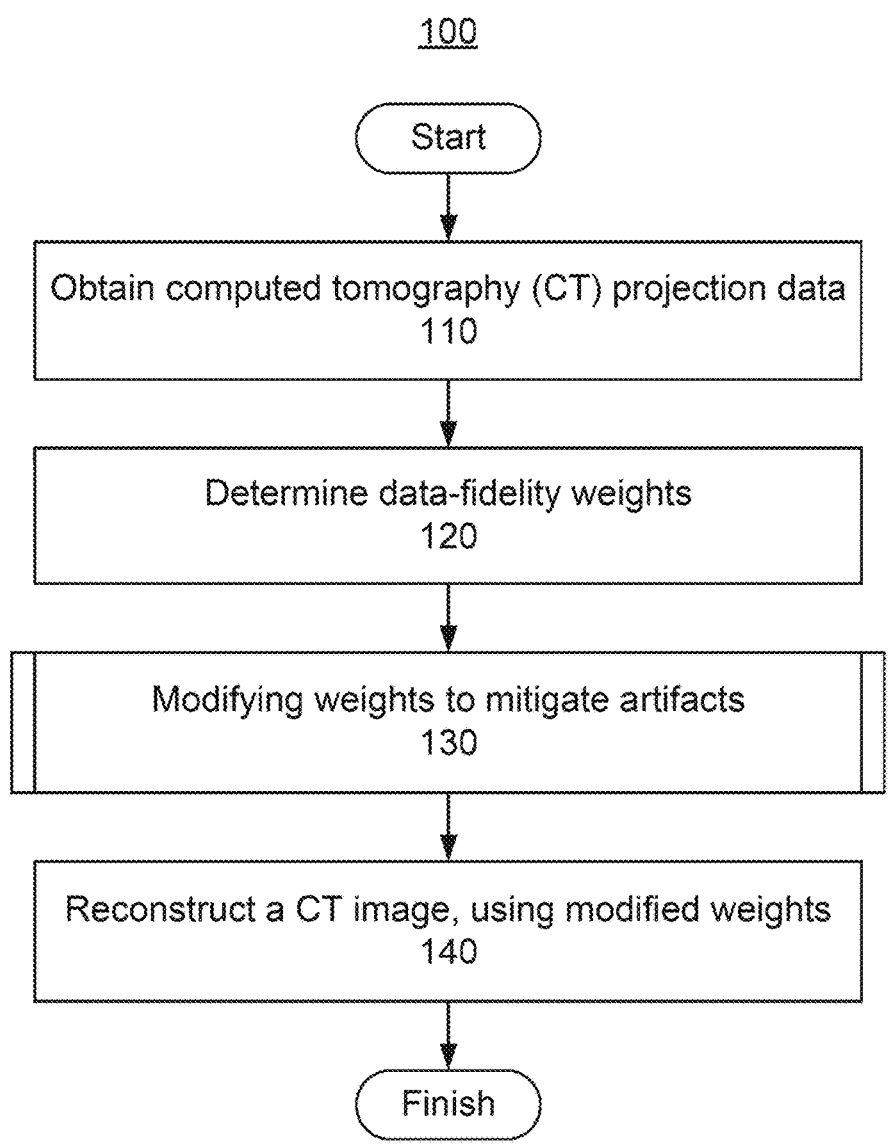
FIG. 4 shows a flow diagram of a method of reconstructing an image from projection data using IR with modified weights, according to one implementation.

To balance the streak artifacts of unweighted IR reconstruction with the anisotropic and peripheral artifacts of weighted IR reconstruction, a compromise method can be used that modifies the weights to balance the trade-offs between the streak artifacts and the anisotropic and peripheral artifacts. FIG. 4 shows method 100 to determine modified weights and then perform IR using the modified weights.

In step 110 of method 100, computed tomography (CT) projection data is obtained, e.g., either from performing a CT scan or by recalling previously stored projection data from memory.

In step 120 of method 100, the data-fidelity weight factors are determined. For example, the data-fidelity weights W can include a statistical weight matrix $W_s$, which represents the uncertainty of the respective projection data (e.g., the standard deviation of the measured irradiance at each pixel). When the noise on each pixel is uncorrelated with the other pixels and projection angles, the statistical weighting matrix will be diagonal. For example, the SNR can be determined for each pixel by dividing the measured amplitude of the pixel by a combination of a Poisson noise contribution corresponding to the measured amplitude of the pixel and a predetermined dark noise value of the pixel. The dark noise value can be determined, for example, by a calibration process. Any known method of determining the statistical weight matrix $W_s$ can be used.

The redundancy weights can be determined using any known reconstruction method. For example, the redundancy weights can be the Parker weights for a half-scan reconstruction, or any other short-scan redundancy weights can be used. Other weights can include calibration weights accounting for pixel-dependent gain factors or other calibrations, for example.

In process 130 of method 100, the weight matrix is modified to trade-off the effects of the streak artifacts and the anisotropic and peripheral artifacts. For example, the statistical weight $W_s$ can be modified to generate modified weights Wc, which are used in place of the statistical weight $W_s$. The use of modified weights Wc can decrease the representation of the peripheral rays in the reconstructed image, making the weights of each pixel less polarized, that is. The modified weights Wc can be determined as $$Wc=F(W_s),$$

wherein F can be any function including a polynomial, a log function, etc. For example, F can be a polynomial function, which is given by $$Wc=W_s^p, 0<p<1$$

A value of p=0 would reduce the modified weights to the case of IR with no statistical weight, whereas a value of p=1 would reduce the modified weights to the case of IR with statistical weights $W_s$. For values 0<p<1, the modified weights mitigate streak artifacts (although perhaps not as well as when p=1) while simultaneously mitigating the anisotropic and peripheral artifacts (although perhaps not as well as when p=0).

In step 140 of method 100, the weights W using the modified weights Wc in place of the statistical weights Ws are used in IR to reconstruct an image from the projection data. Any known method can be used to solve for the argument minimizing the objective/cost function.

Similar results to those achieved using the modified weights might also be achieved using a specially tailored regularizer together with statistical weights to mitigate both the streak artifacts and the anisotropic and peripheral artifacts. Generating a tailored regularizer can require significantly more computational resources than the relatively simple computation used to modify the statistical weights. Moreover, results obtained using a tailored regularizer suffer when applied to low-dose IR in which streak artifacts can still observed. Accordingly, in contrast to tailored regularizers, the disclosed modified-statistical-weights method simultaneously mitigates streak artifacts and anisotropic and peripheral artifacts, while minimizing additional requirements for computational resources.

Figure 5A:
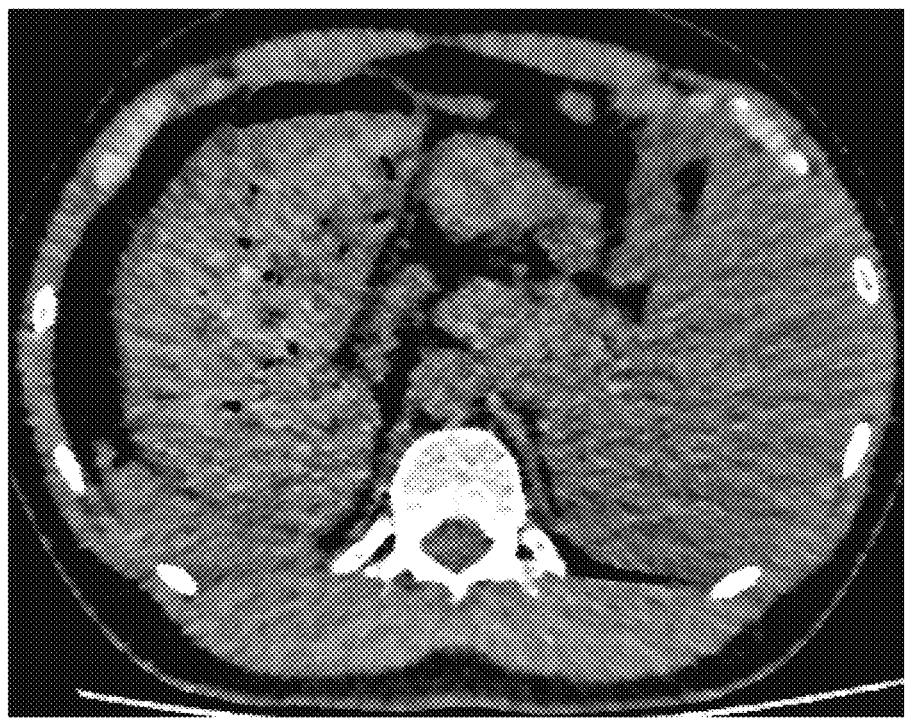
FIG. 5A shows a reconstructed image using IR with modified weights having p=0.3, according to one implementation.
Figure 5B:
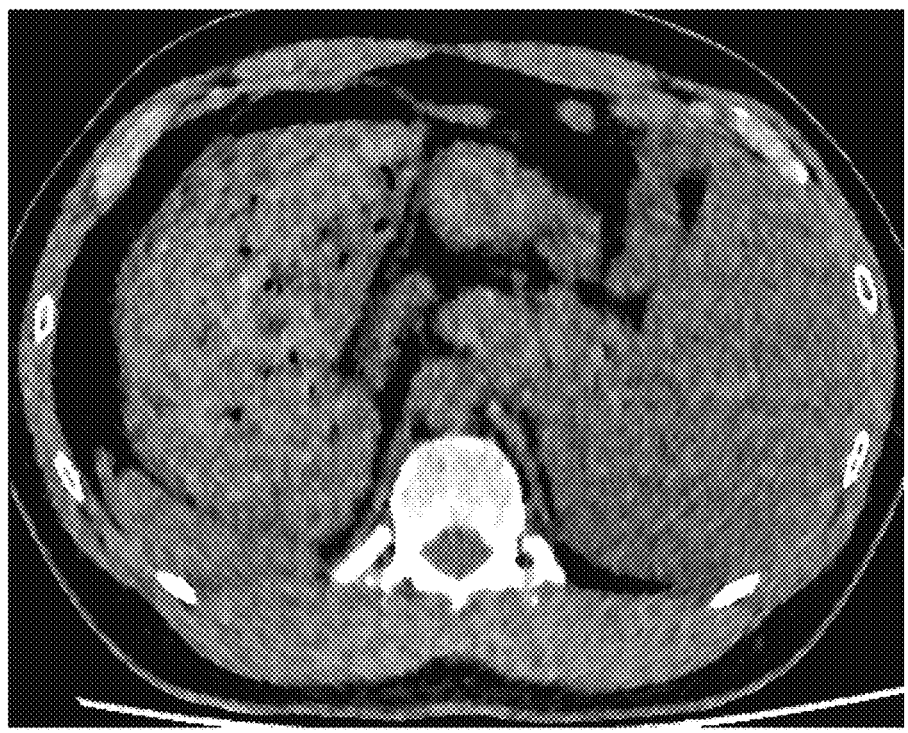
FIG. 5B shows a reconstructed image using IR with modified weights having p=1.0, according to one implementation.
Figure 5D:
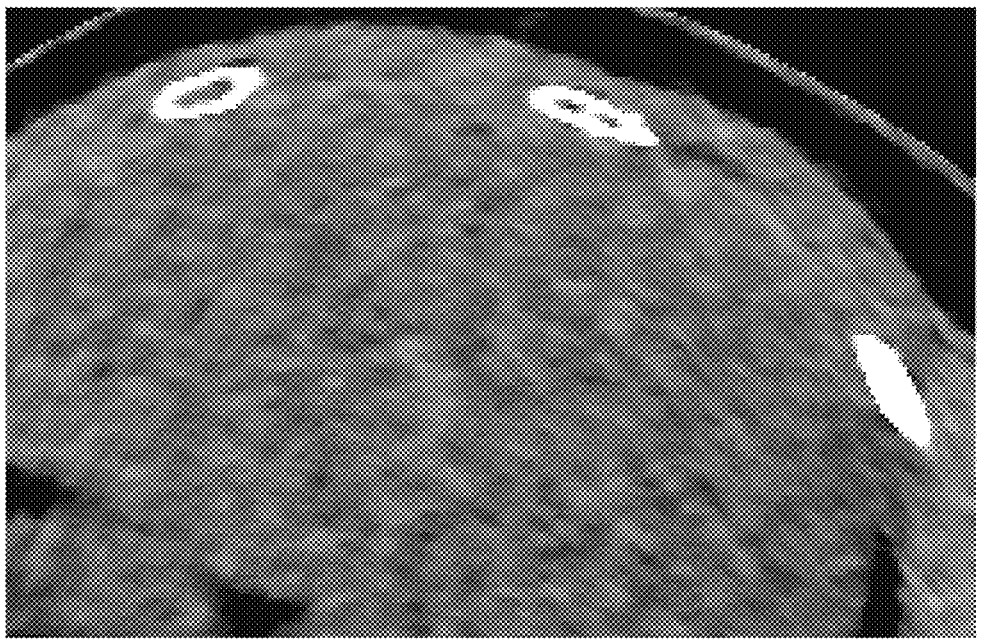
FIG. 5D shows a close up of the reconstructed image from FIG. 5B.
Figure 5C:
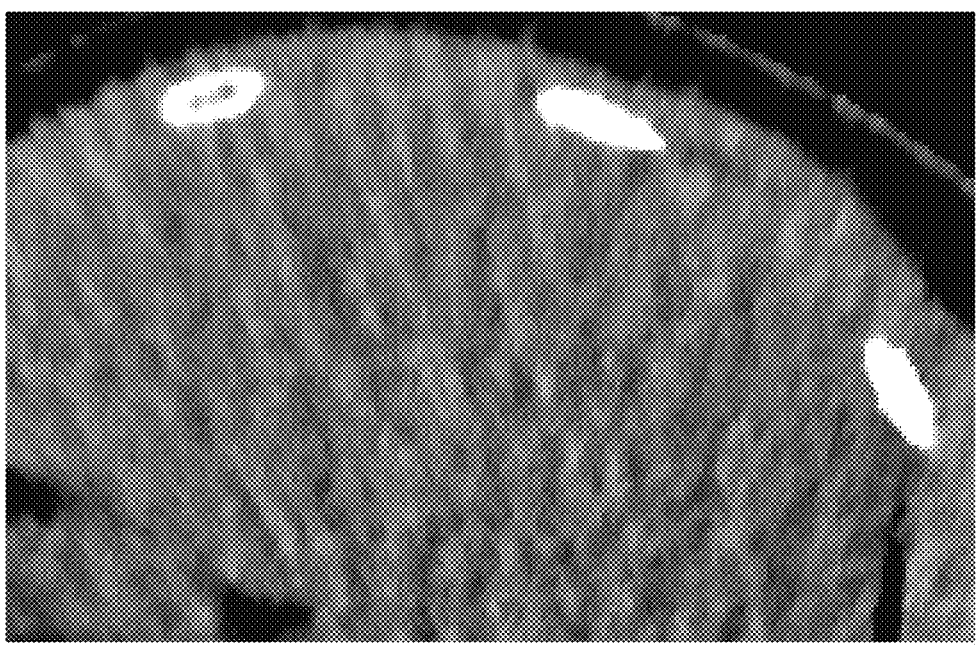
FIG. 5C shows a close up of the reconstructed image from FIG. 5A.

FIGS. 5A and 5B respectively show reconstructed images for the modified cases of p=0.3 and p=1. The case p=1 is identical to IR using the unmodified statistical weights, as shown in FIG. 1B. FIG. 5A shows some streak artifacts, but less than those observed in FIG. 1A, corresponding to a case of p=0 (i.e., no statistical weighting). Also notable in FIGS. 5A and 5B is that less anisotropic and peripheral artifacts are observed in FIG. 5A than in FIG. 5B. FIGS. 5C and 5D show close up images of FIGS. 5A and 5B respectively.

Figure 6:
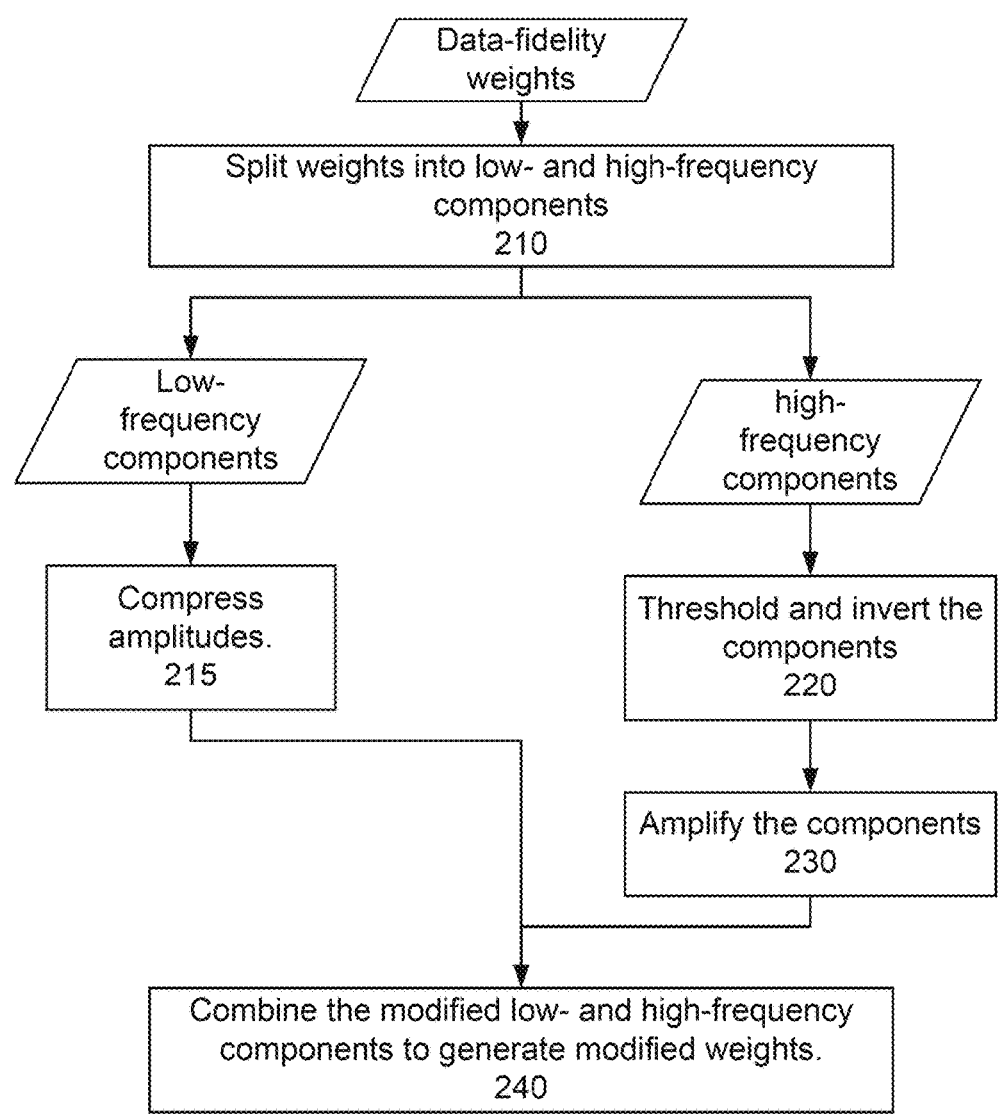
FIG. 6 shows a flow diagram of a method of determining modified weights by splitting into high- and low-frequency components, according to one implementation.

FIG. 6 shows a flow diagram of method 200 for modifying the statistical weights. Method 200 treats the low-frequency and high-frequency components of the statistical weights differently. Method 200 can replace process 130 in method 100 to create a frequency-dependent modification of the statistical weights.

It is observed that the low frequency component of statistical weights contribute to the anisotropic artifacts, whereas high-frequency components are related to the streak artifacts. Thus, to address both types of artifacts, the statistical weights can be separated into low- and high-frequency components in order to compress the low-frequency components of the statistical weights while preserving/amplifying the amplitudes (and sometimes inverting the amplitudes, as explained later) of the high-frequency components of statistical weights. Thus, through disparate treatment of the low- and high-frequency components, the various artifacts can each be more effectively mitigated.

In step 210 of method 200, the data-fidelity weights of step 120 are split into high-frequency components and low-frequency components. Rather than a more conventional split, wherein the total weights are a superposition of the high-frequency components and the low-frequency components, the frequency components can be separated into conventional low-frequency components, and the high-frequency component can be represented by the ratio between the total weights and the low-frequency components. That is the frequency component split of statistical weight Ws can be expressed as $$W_S = W_{sL} \cdot W_{sH}$$

wherein $W_{sL}$ is the low-frequency components of $W_s$ and $W_{sH}$ is the high-frequency components of $W_S$.

Figure 7A:
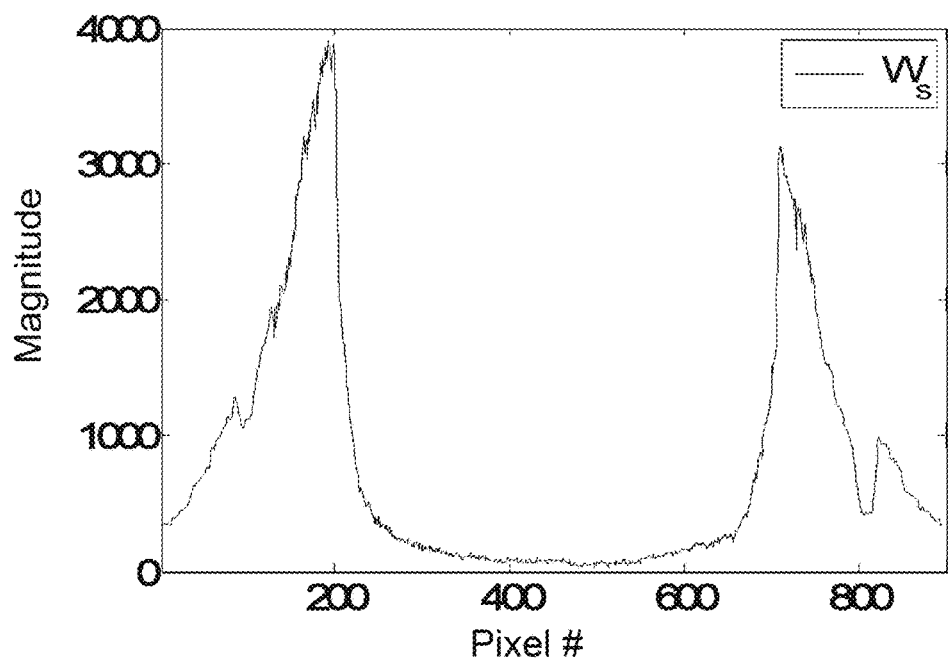
FIG. 7A shows a plot of data-fidelity weights, according to one implementation.
Figure 7B:
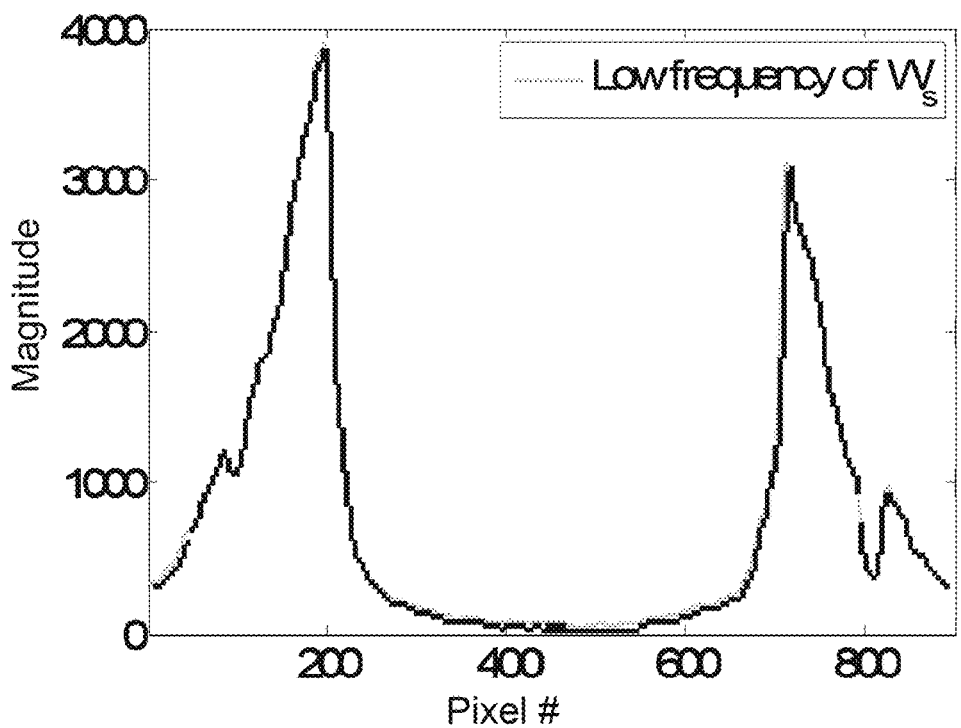
FIG. 7B shows a plot of low-frequency components of the data-fidelity weights, according to one implementation.
Figure 7C:
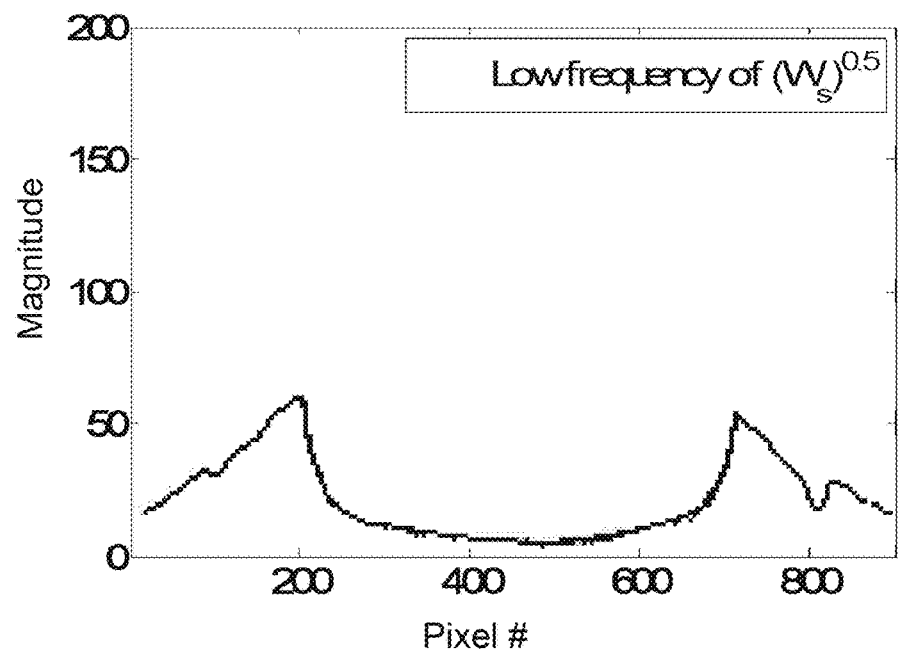
FIG. 7C shows a plot of compressed low-frequency components of the data-fidelity weights, according to one implementation.
Figure 7D:
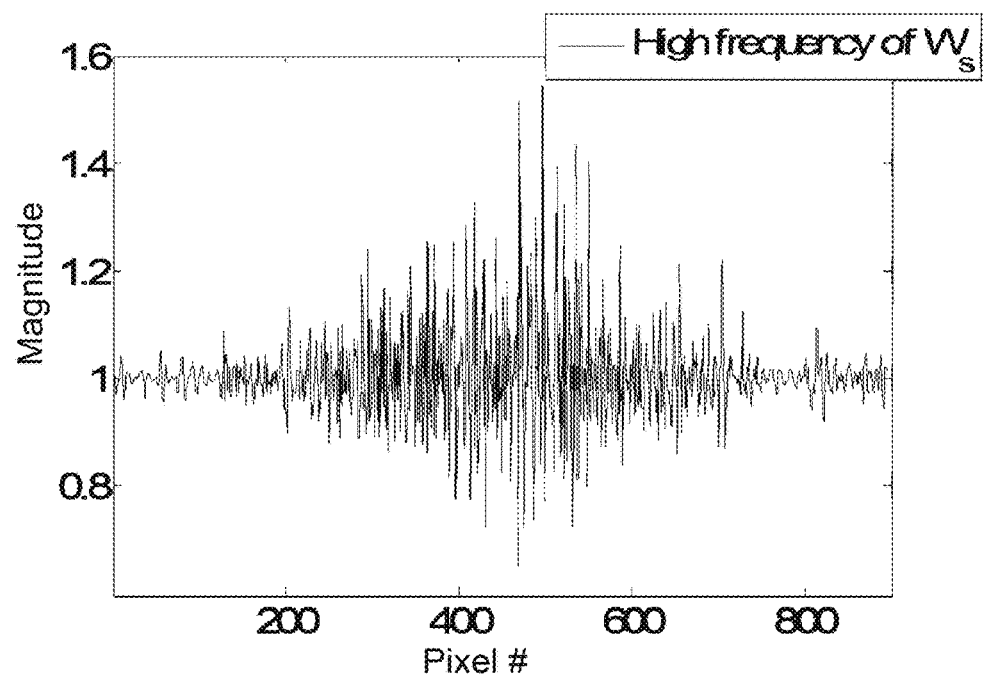
FIG. 7D shows a plot of high-frequency components of the data-fidelity weights, according to one implementation.

FIG. 7A shows a plot of statistical weight Ws as a function of pixel number. FIGS. 7B and 7D respectively show low- and high-frequency components of the statistical weight Ws. The frequency split can be performed in either the spatial or the frequency domain, and the low-frequency components can be determined using a low-pass filter $\tilde{F}$, which is a Savitzky-Golay filter, a Gaussian filter, or any other known low-pass filter. Thus, the low-frequency components can be determined as by $$W_{sL} = \tilde{F}(W_s),$$

and the high-frequency components can be determined $$W_{sH} = \frac{W_s}{\tilde{F}(W_s)}.$$

After determining the high- and low-frequency components, the two components can then be separately operated on to better address the various types of artifacts. For example, the high- and low-frequency components can be separately compressed/magnified using functions G and F respectively, which can be empirically optimized to minimize the artifacts in the reconstructed image. That is, the modified weights can be expressed by $$W_C = F(W_{sL}) \cdot G(W_{sH})$$

wherein F and G are two functions. For example, F and G can be polynomial functions, which are given by $$W_C = (\tilde{F}(W_s))^p \cdot \left(\frac{W_s}{\tilde{F}(W_s)}\right)^q,$$

wherein $p \geq 0$ and $q \geq 0$.

Thus, if $p<1$ the low-frequency components are compressed, and if $p>1$ the low-frequency components are magnified. Similarly, if $q<1$ high-frequency components are compressed, and if $q>1$ the high-frequency components are magnified.

In step 215 of method 200, the low-frequency components are compressed. For example, the low-frequency components can be operated on by a function F that is a polynomial of order less than 1 (e.g., $F(x)=x^p$). FIG. 7C shows a plot of low-frequency components after they have been compressed using function F, wherein F is a polynomial function of order $p=0.5$.

In step 220 of method 200, a threshold-and-invert step is applied to the high-frequency components. The threshold-and-invert step takes the inverse of each high-frequency component that is above a predefined threshold (e.g., a threshold of one). The threshold-and-invert step is guided by the insight that locally across small spatial regions both the intensity of the X-ray ray beam from the X-ray source and the attenuation due to the subject will vary smoothly. Thus, the X-ray radiation incident on neighboring pixels will likely have experienced similar attenuation and should also be smooth. Thus, differences between counts measured on adjacent pixels are likely due to statistical variations rather than representing actual variations in the relative intensity. These statistical variations among neighboring pixels are expressed by deviations from a value of one in the high-frequency components. In the case of high-frequency components having values less than one, pixels exhibiting large deviation from the local mean are assigned lower statistical weights for IR, consistent with the insight that these pixel represent larger statistical variation and are therefore to be trusted less.

However, contrary to the insight that high-frequency components greater than one are also likely to be statistical aberrations and therefore should be trusted less, pixels corresponding to high-frequency components with higher values are conventionally considered to have higher SNRs and are therefore given greater weight in the IR. The threshold-and-invert step corrects for this tendency of overvaluing high signal pixels that represent statistical aberrations relative to their neighboring pixels.

Thus, using the threshold-and-invert step, pixels with high-frequency components deviating significantly from one are assigned lower statistical weights based on the reasoning that large statistical variations from one for the high-frequency components would be unreliable whether they are much greater than one or much less than one. Accordingly, the threshold-and-invert step takes the inverse of those high-frequency components greater than the threshold (e.g., the threshold can be one) in order to represent a greater trust for pixels with high-frequency components close to one and less trust in those high-frequency components far from one, regardless of whether the high-frequency components are much greater than or much less than one.

That is, those rays with fewer counts than a local mean are presumed to be noisy, and those rays are accordingly weighted less than neighboring rays that are closer to the local mean. Similarly, rays with larger counts than a local mean are also presumed to correspond to noisy rays, and, after the threshold-and-invert step, are also weighted less than neighboring rays that are closer to the local mean. The result of the threshold-and-invert step can be expressed as $$TI(W_{sH}) = \begin{cases} W_{sH}, & \text{if } W_{sH} < 1 \text{ (low counts ray)} \\ 1/W_{sH}, & \text{if } W_{sH} \geq 1 \text{ (high counts ray)} \end{cases},$$

or $$TI(W_{sH}) = \begin{cases} \left(\dfrac{W_s}{\tilde{F}(W_s)}\right), & \text{if } W_s < \tilde{F}(W_s) \text{(low counts ray)} \\ \left(\dfrac{\tilde{F}(W_s)}{W_s}\right), & \text{if } W_s \geq \tilde{F}(W_s) \text{(high counts ray)} \end{cases}$$

Figure 7E:
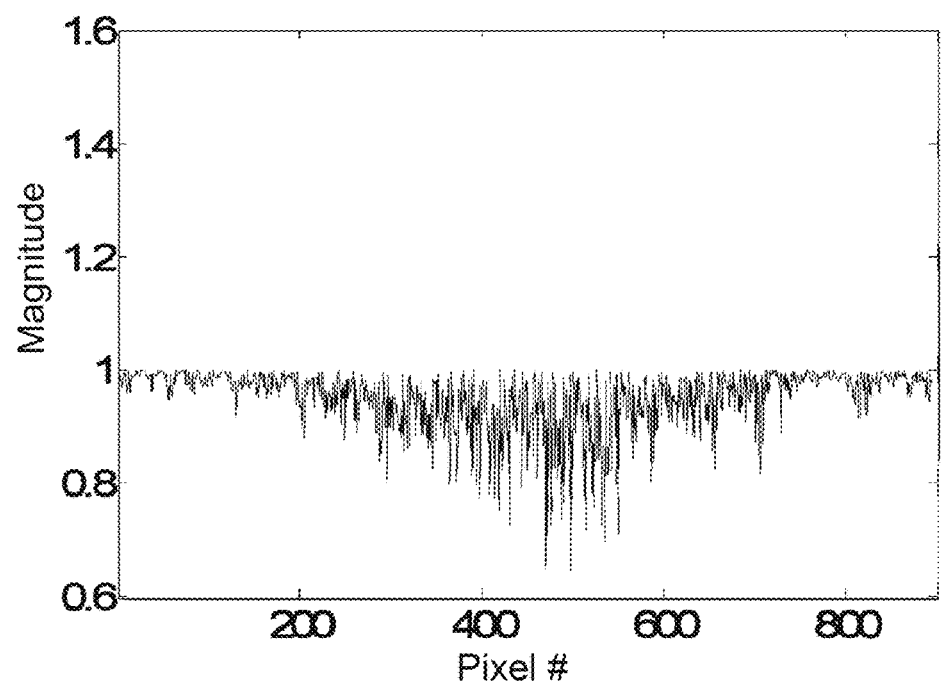
FIG. 7E shows a plot of high-frequency components of the data-fidelity weights after a threshold-and-invert step, according to one implementation.

FIG. 7E shows the high-frequency components of FIG. 7D after performing the threshold-and-invert step using a threshold value of one. In certain implementations, the threshold-and-invert step can be omitted.

Figure 7F:
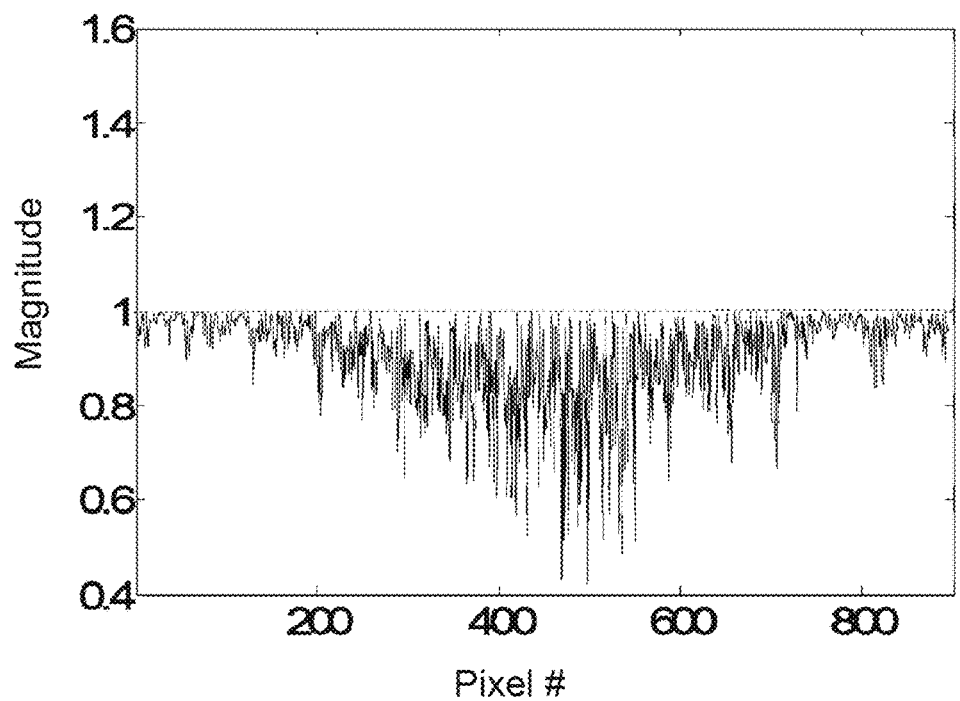
FIG. 7F shows a plot of high-frequency components of the data-fidelity weights after amplification and a threshold-and-invert step, according to one implementation.

In step 230 of method 200, the result of the step 220 is amplified or compressed using the function G. For example, the high-frequency components can be operated on by a function G that is a polynomial (e.g., $G(x)=x^q$). If the high-frequency components are to be amplified or maintained constant, then $q \geq 1$. Otherwise, $q<1$ and the high-frequency components are compressed. FIG. 7F shows high-frequency components from FIG. 7E after amplification using a polynomial function with q=2.

In step 240 of method 200, the modified low- and high-frequency components are combined to generate the modified weights $$W_C = F(W_{sL}) \cdot G(W_{sH}).$$

When step 220 is not omitted the modified weights can be expressed as $$W_C = \begin{cases} (\tilde{F}(W_s))^p \cdot \left(\dfrac{W_s}{\tilde{F}(W_s)}\right)^q, & \text{if } W_s < \tilde{F}(W_s) \text{(low counts ray)} \\ (\tilde{F}(W_s))^p \cdot \left(\dfrac{\tilde{F}(W_s)}{W_s}\right)^q, & \text{if } W_s \geq \tilde{F}(W_s) \text{(high counts ray)} \end{cases}$$

Figure 7G:
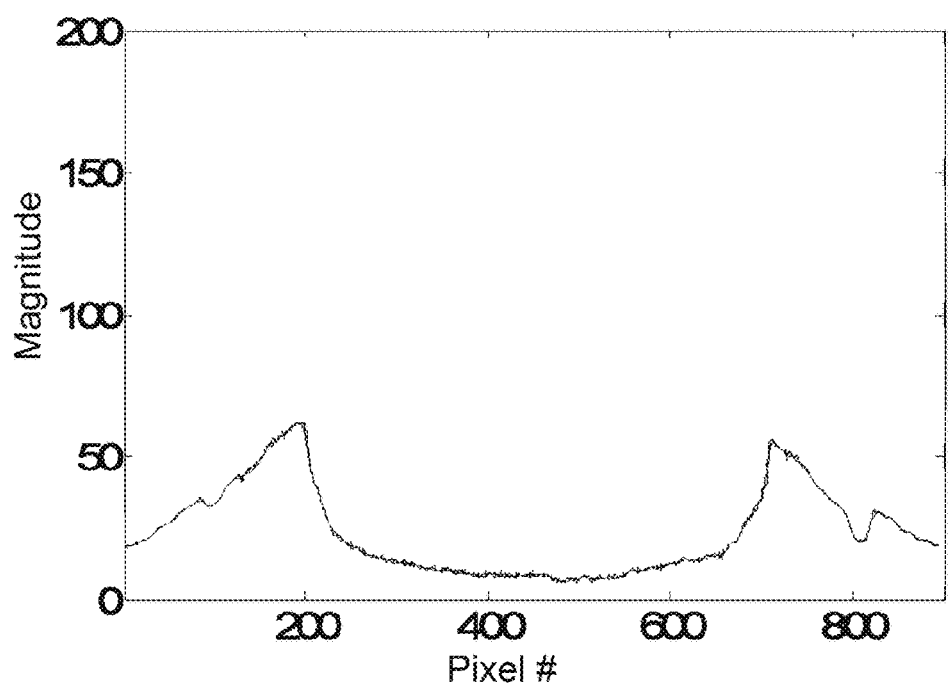
FIG. 7G shows a plot of a combination of the modified low-frequency components with the modified high-frequency components, according to one implementation.

FIG. 7G shows the modified weights for cases both with and without the threshold-and-invert step. In FIG. 7G, the polynomial functions applied to the low- and high-frequency components respectively were if the order p=0.5 and q=1.

Figure 8:
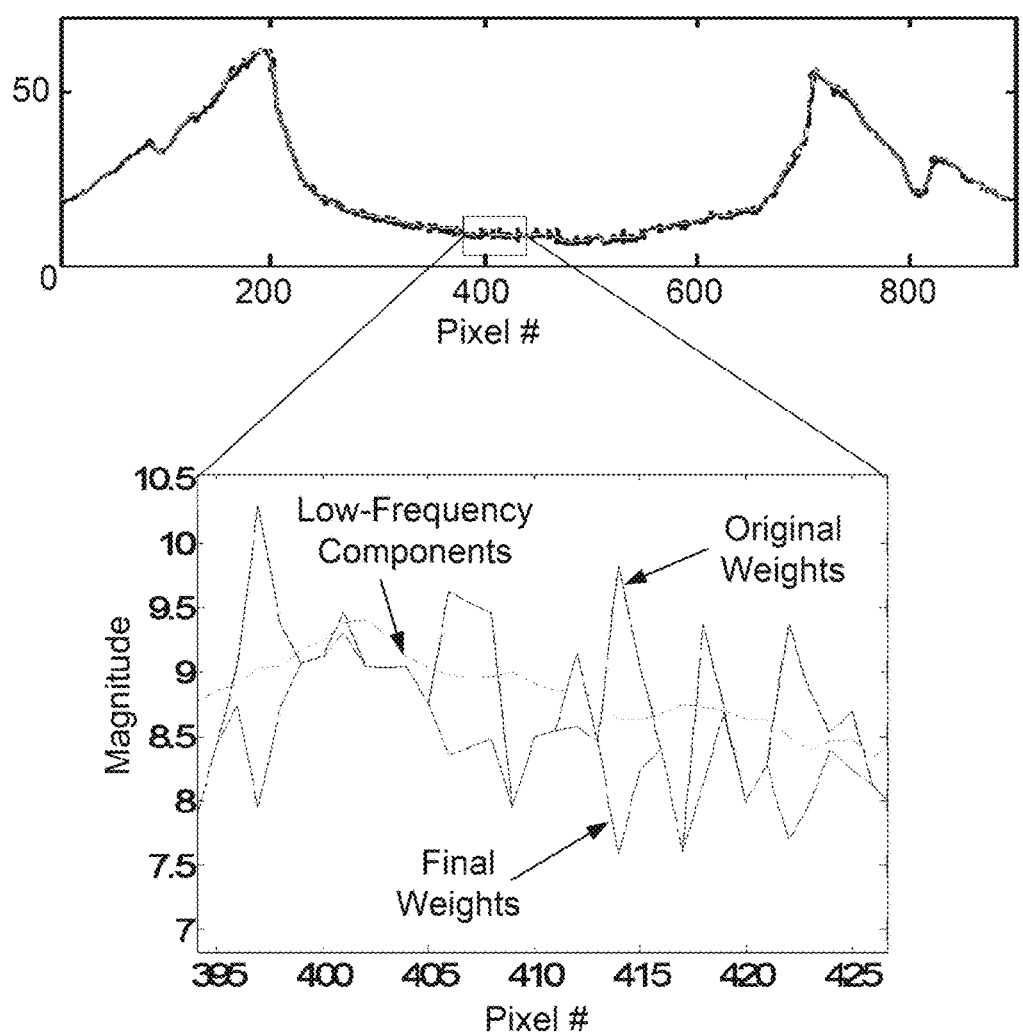
FIG. 8 shows a close up of the combined modified weights from FIG. 7G.
Figure 9A:
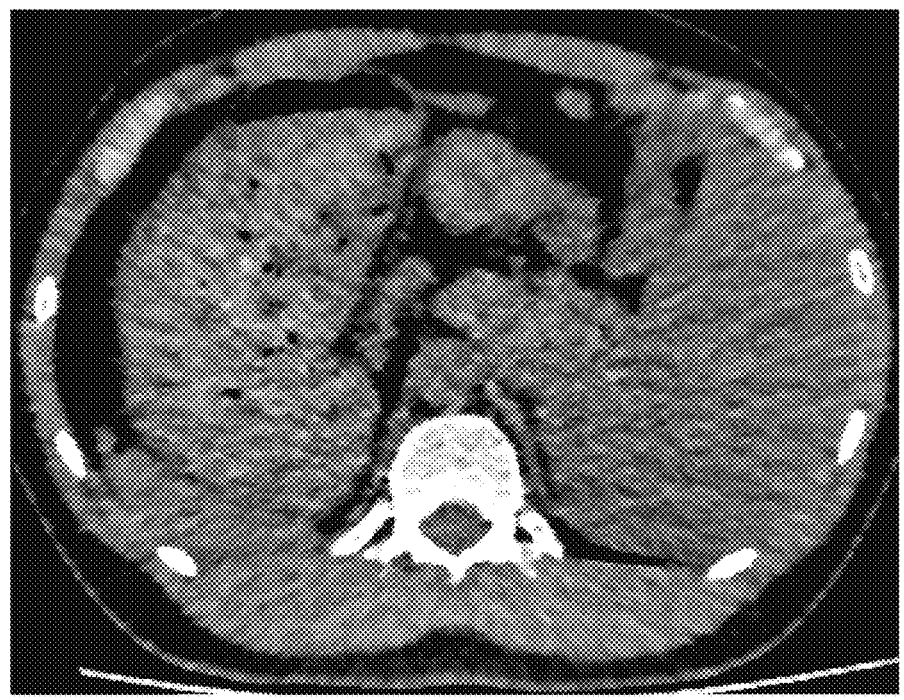
FIG. 9A shows a plot of a reconstructed image without using frequency splitting and using modified weights with p=q=0.1, according to one implementation.
Figure 9B:
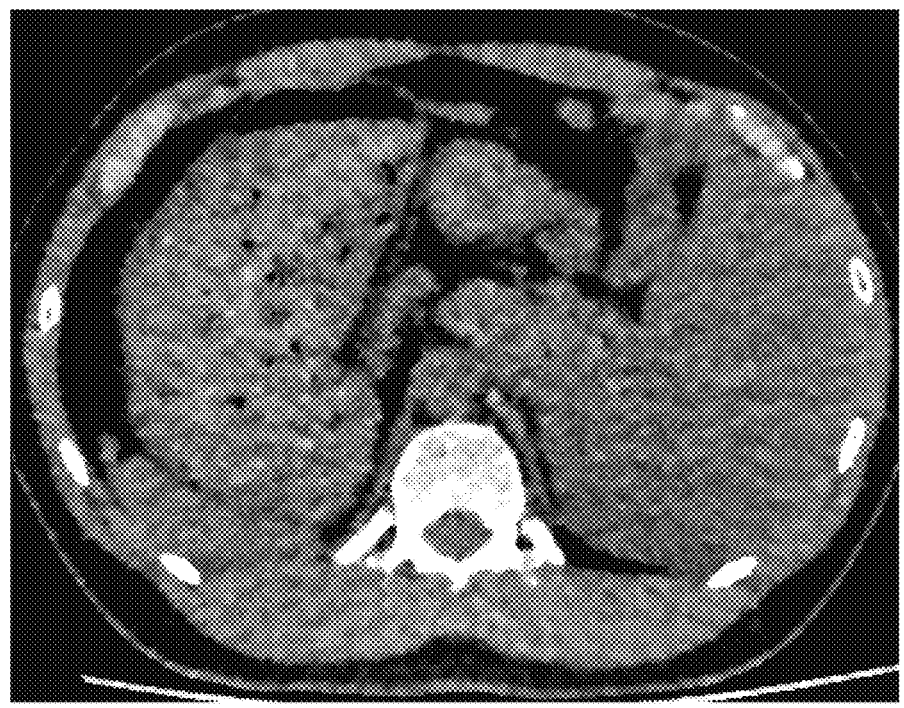
FIG. 9B shows a plot of a reconstructed image using frequency splitting with modified weights according to p=1 and q=0.1 and using a threshold-and-invert step, according to one implementation.
Figure 9C:
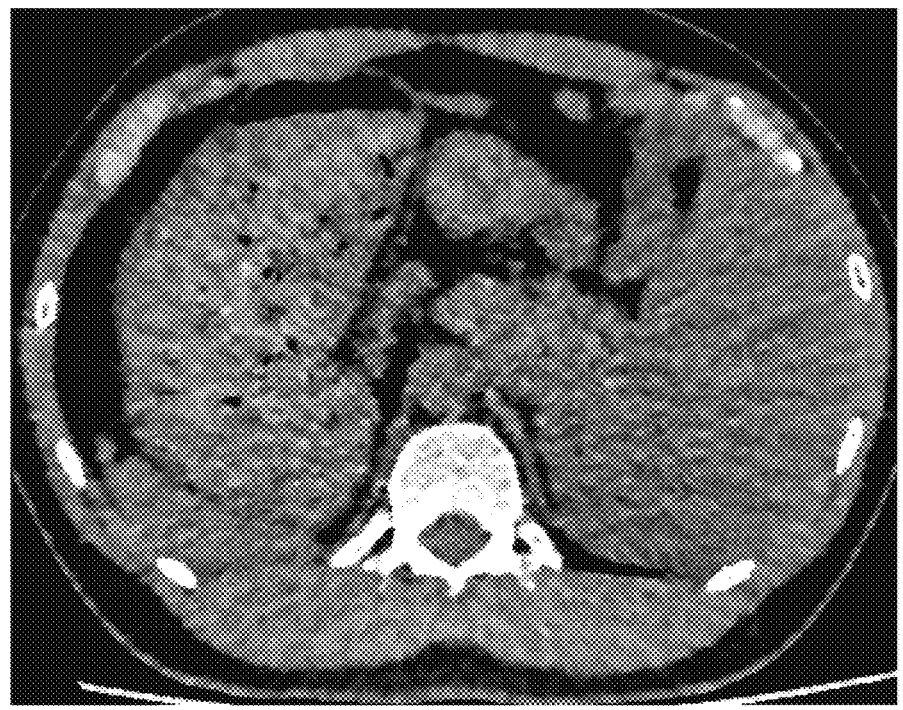
FIG. 9C shows a plot of a reconstructed image without using frequency splitting and using modified weights with p=q=0.3, according to one implementation.
Figure 9D:
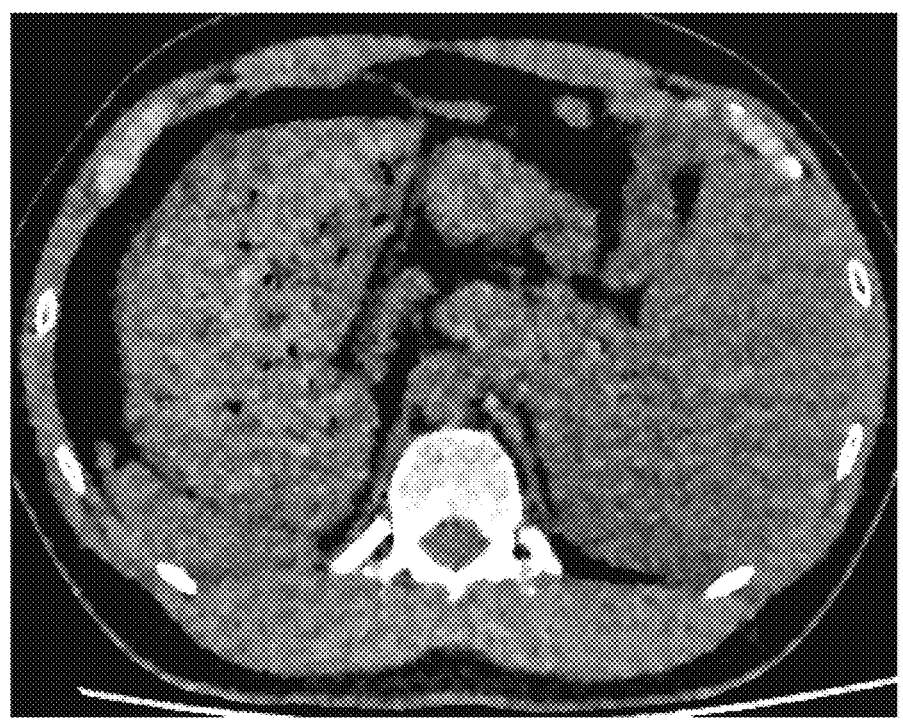
FIG. 9D shows a plot of a reconstructed image using frequency splitting with modified weights according to p=1 and q=0.3 and using a threshold-and-invert step, according to one implementation.
Figure 9E:
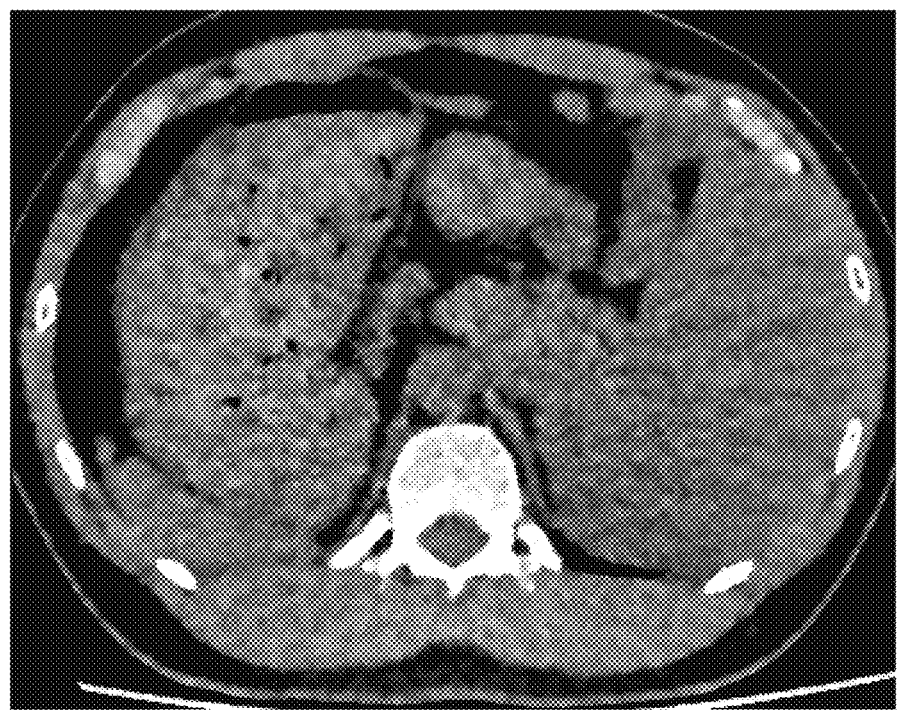
FIG. 9E shows a plot of a reconstructed image without using frequency splitting and using modified weights with p=q=0.5, according to one implementation.
Figure 9F:
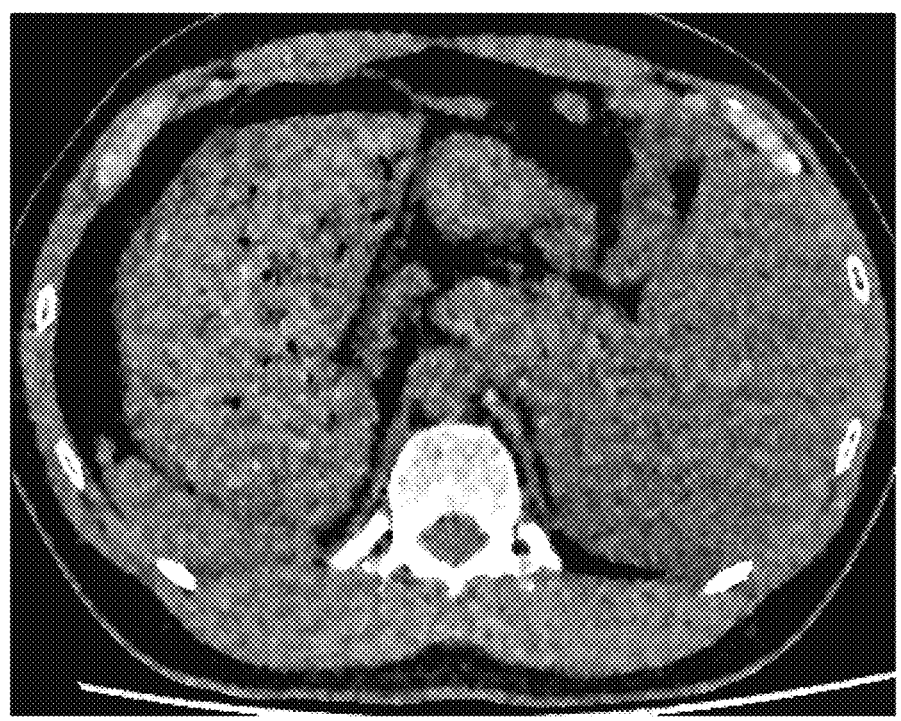
FIG. 9F shows a plot of a reconstructed image using frequency splitting with modified weights according to p=1 and q=0.5 and using a threshold-and-invert step, according to one implementation.
Figure 9G:
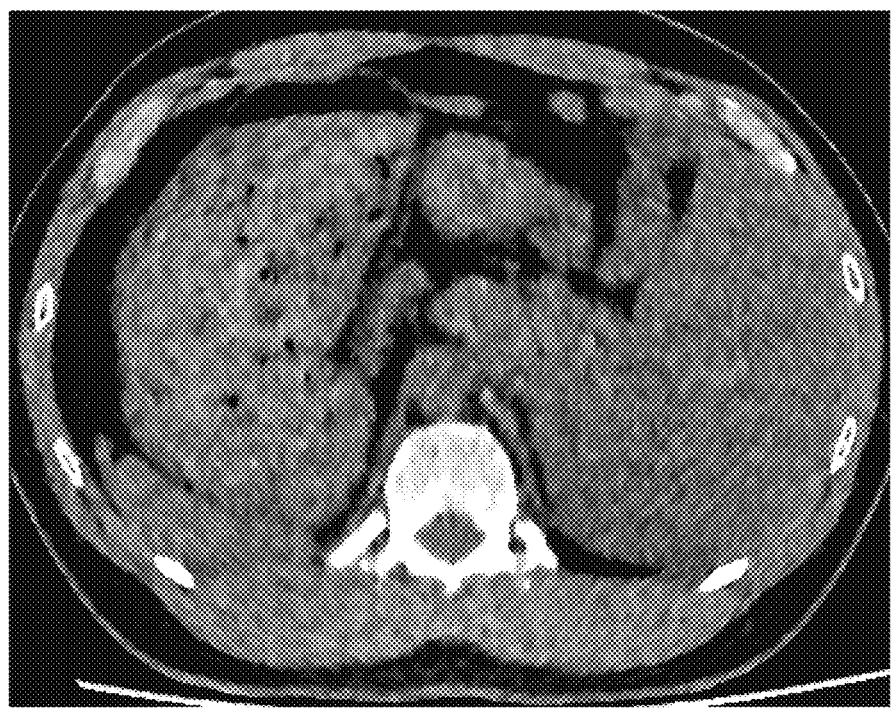
FIG. 9G shows a plot of a reconstructed image without using frequency splitting and using modified weights with p=q=1.0, according to one implementation.
Figure 9H:
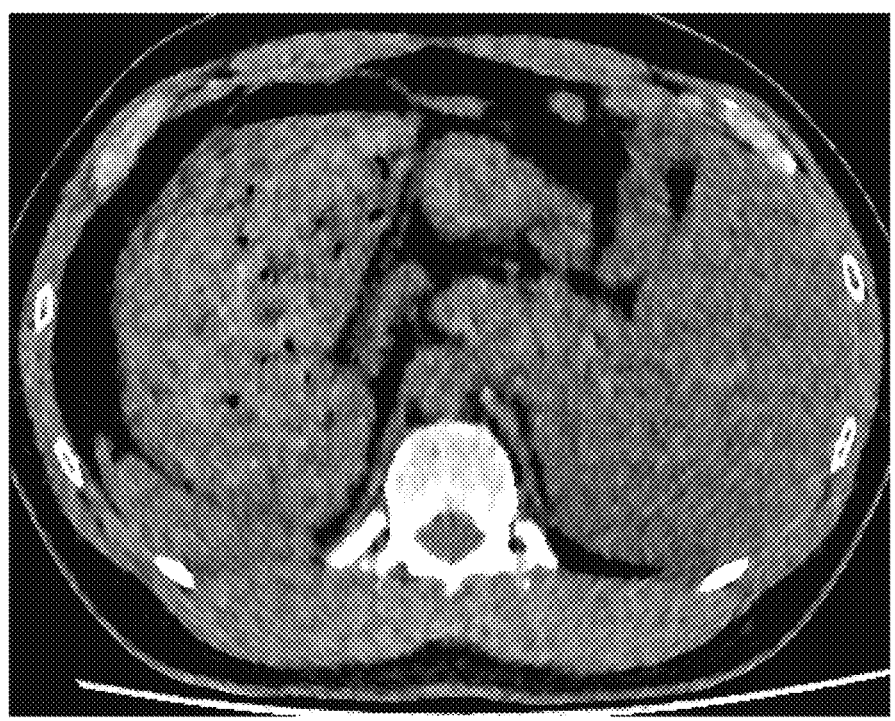
FIG. 9H shows a plot of a reconstructed image using frequency splitting with modified weights according to p=q=1.0 and using a threshold-and-invert step, according to one implementation.

FIG. 8 shows a close up of the modified weights in FIG. 7G. As can be seen in FIG. 8, those statistical weights that are greater than the local average (as represented by the low-frequency components of the weights) are converted to modified weights that are below the original low-frequency components.

FIGS. 9A, 9B, 9C, 9D, 9E, 9F, 9G, and 9H represent reconstructed images using method 100 and method 200 that are operated on using polynomial functions F and G of order p and q respectively. FIGS. 9A, 9C, 9E, and 9G were reconstructed with modified weights determined without dividing into low- and high-frequency components, whereas 9B, 9D, 9F, and 9H use modified weights determined by separating the weights into low- and high-frequency components and performing the threshold-and-invert step. It is noted that performing compression of the weights without frequency splitting and using a polynomial of order p produces the same modified weights as using frequency splitting while omitting the threshold-and-invert step and using compression functions that are polynomial having identical orders p=q. The images in FIGS. 9A, 9C, 9E, and 9G are reconstructed using polynomial values of p=q=0.1, p=q=0.3, p=q=0.5, and p=q=1, respectively. The images in 9B, 9D, 9F, and 9H are each reconstructed using a threshold-and-invert step for the high-frequency components and using a polynomial value of q=1 (i.e., no compression for the high-frequency components), and the low-frequency components are compressed using polynomial values of p=0.1, p=0.3, p=0.5, and p=1, respectively. As shown in FIGS. 9A, 9B, 9C, 9D, 9E, 9F, 9G, and 9H, method 200 better mitigates both streak artifacts and anisotropic and peripheral artifacts than does the frequency independent method.

Figure 10A:
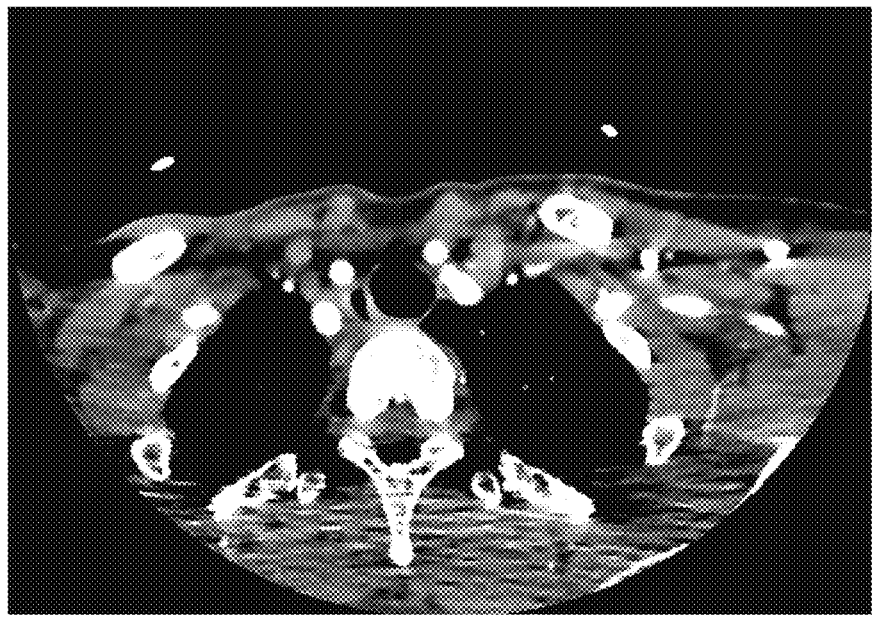
FIG. 10A shows a plot of a reconstructed image without using frequency splitting, using modified weights with p=q=0.1, and using a regularization factor of $\beta$=2, according to one implementation.
Figure 10B:
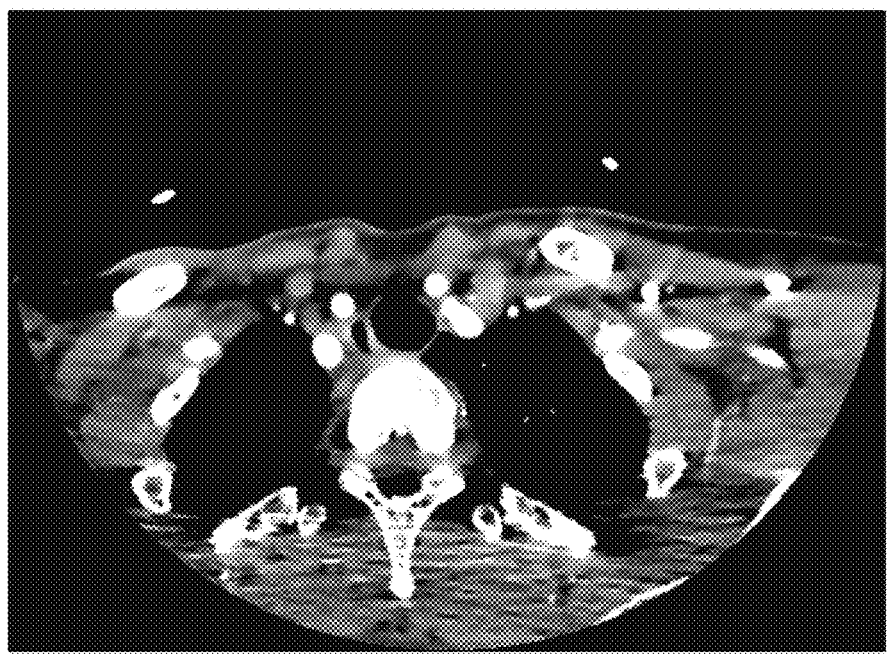
FIG. 10B shows a plot of a reconstructed image using frequency splitting with modified weights according to p=q=0.1, using a threshold-and-invert step, and using a regularization factor of $\beta$=2, according to one implementation.

FIGS. 10A and 10B provide additional comparison of the methods described herein. FIG. 10A shows an image reconstructed using modified weights in which the polynomial values were p=q=0.1 and the threshold-and-reverse step is omitted. FIG. 10B shows an image reconstructed using modified weighting in which the polynomial values were p=q=0.1 and the threshold-and-reverse step is applied. The images in FIGS. 10A and 10B were both generated using a regularization factor of β=2.

Figure 11A:
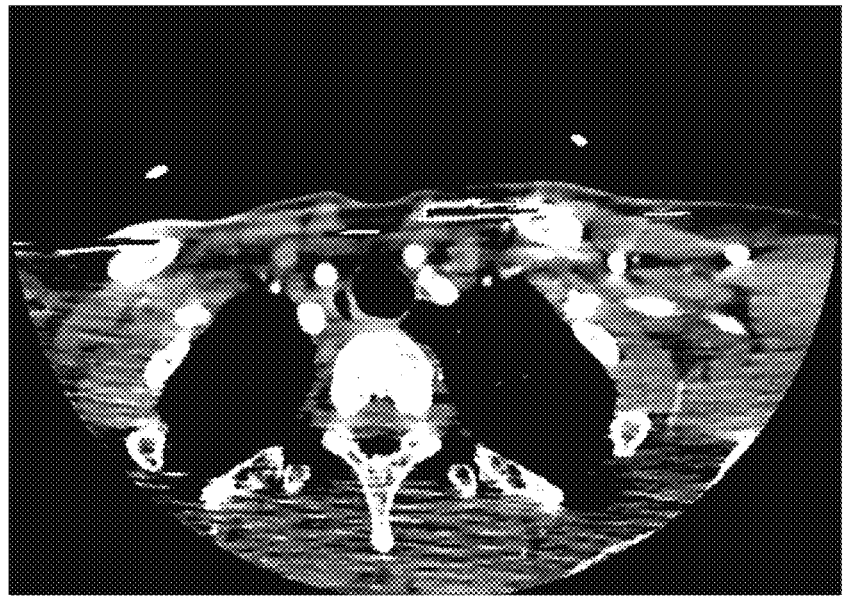
FIG. 11A shows a plot of a reconstructed image using frequency splitting without a threshold-and-invert step, using modified weights with p=1 and q=0.1, and using a regularization factor of $\beta$=1.5, according to one implementation.
Figure 11B:
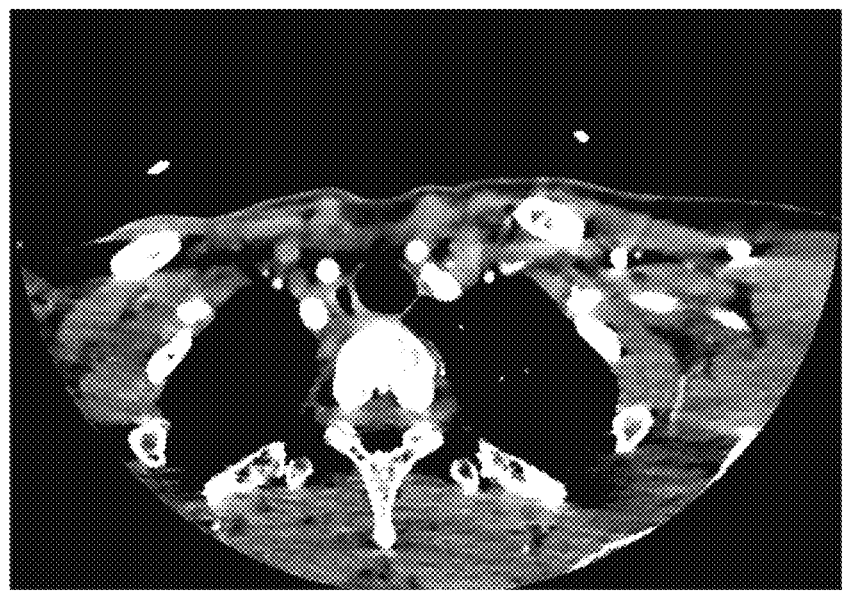
FIG. 11B shows a plot of a reconstructed image using frequency splitting with modified weights according to p=1 and q=0.1, using a threshold-and-invert step, and using a regularization factor of $\beta$=1.5, according to one implementation.

FIGS. 11A and 11B also provide additional comparison of the methods described herein. FIG. 11A shows an image reconstructed using modified weighting in which the polynomial values were p=0.1 and q=1.0, and the threshold-and-reverse step is omitted. FIG. 11B shows an image reconstructed using modified weighting in which the polynomial values were p=0.1 and q=1.0 and the threshold-and-reverse step is applied. The images in FIGS. 11A and 11B were both generated using a regularization factor of β=1.5.

In FIGS. 10A, 10B, 11A, and 11B, it can be observed that applying the threshold-and-reverse step generates images having higher image quality. Additionally, it can be observed that compressing the low-frequency components, while leaving the high-frequency components uncompressed generates better image quality.

Figure 12:
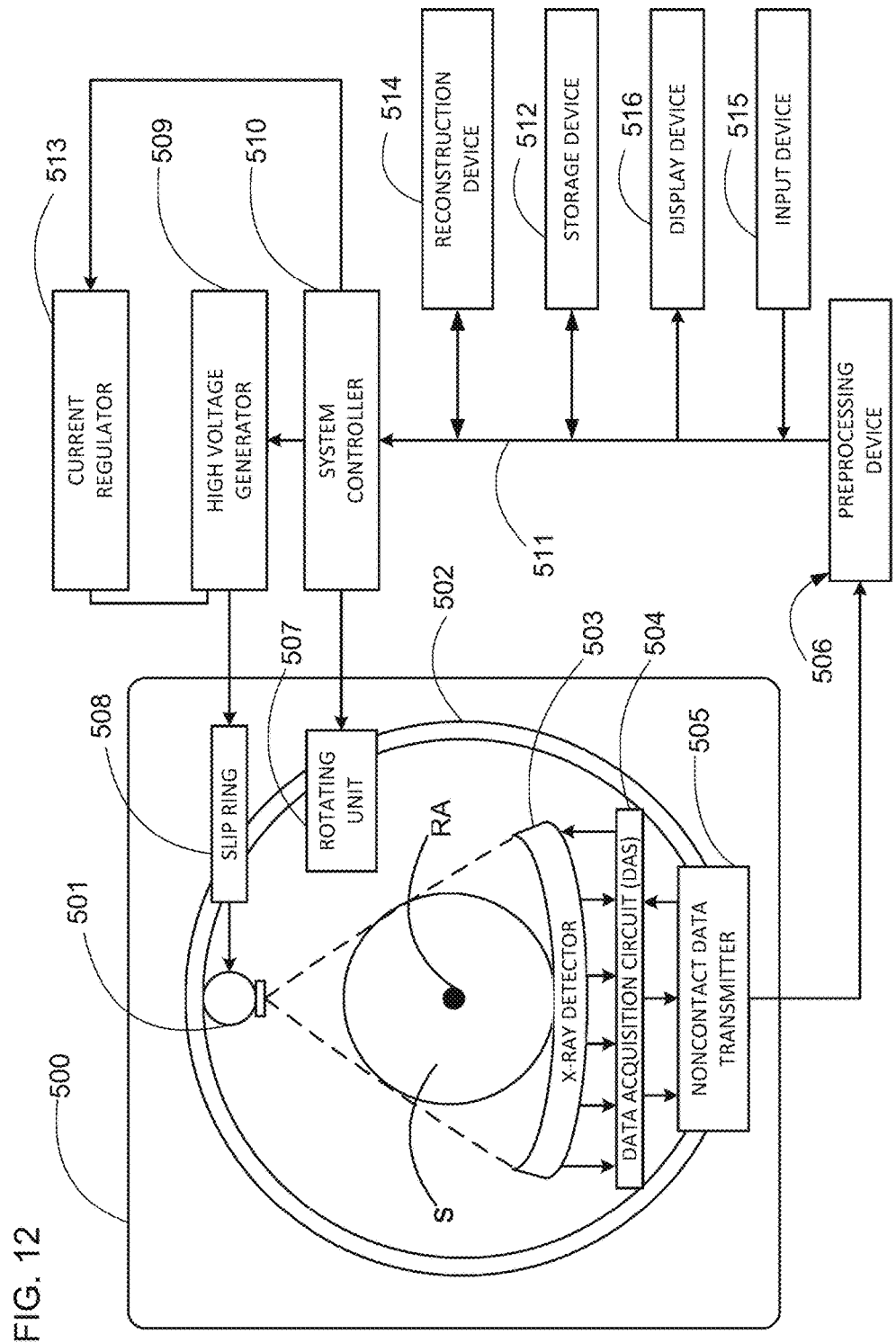
FIG. 12 shows a schematic of an implementation of a CT scanner.

FIG. 12 illustrates an implementation of the radiography gantry included in a CT apparatus or scanner. As shown in FIG. 12, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA. A rotating unit 507 rotates the annular frame 502 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR).

The above-described data is sent to a preprocessing device 506, which is housed in a console outside the radiography gantry 500 through a non-contact data transmitter 505. The preprocessing device 506 performs certain corrections, such as sensitivity correction on the raw data. A memory 512 stores the resultant data, which is also called projection data at a stage immediately before reconstruction processing. The memory 512 is connected to a system controller 510 through a data/control bus 511, together with a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object OBJ as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The memory 512 can store the measurement value representative of the irradiance of the X-rays at the X-ray detector unit 503. Further, the memory 512 can store a dedicated program for executing the CT image reconstruction methods, including methods to perform method 100 and method 200 discussed herein.

The reconstruction device 514 can execute the method 100 and the method 200 discussed herein. Further, reconstruction device 514 can execute pre-reconstruction processing image processing such as volume rendering processing and image difference processing as needed.

The pre-reconstruction processing of the projection data performed by the preprocessing device 506 can include correcting for detector calibrations, detector nonlinearities, and polar effects, for example.

Post-reconstruction processing performed by the reconstruction device 514 can include filtering and smoothing the image, volume rendering processing, and image difference processing as needed. The image reconstruction process can be performed using method 100 and/or method 200. The reconstruction device 514 can use the memory to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 512 can be non-volatile, such as ROM, EPROM, EEPROM or FLASH memory. The memory 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The memory 512 can be a hard disk drive, CD-ROM drive, DVD drive, FLASH drive, RAM, ROM or any other electronic storage known in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
   circuitry configured to
      obtain projection data representing an intensity of X-ray radiation detected at a plurality of detector elements,
      determine statistical weights corresponding to respective pixel-intensity values of the projection data,
      modify the statistical weights by generating high-frequency components and low-frequency components of the statistical weights, operating on the low-frequency components using a predefined first function, and operating on the high-frequency components using a predefined second function to generate modified weights, and
      reconstruct an image by minimizing an objective function, which includes the modified statistical weights.

2. The apparatus according to claim 1, wherein the circuitry is further configured to modify the statistical weights by operating on the low-frequency components using the first function, which is a compressing function that decreases relative differences between respective values of the statistical weights.

3. The apparatus according to claim 1, wherein the circuitry is further configured to modify the statistical weights by operating on the low-frequency components using the first function, which is one of a polynomial function and a logarithmic function.

4. The apparatus according to claim 1, wherein the circuitry is further configured to modify the statistical weights by operating on the low-frequency components using the first function, which is a polynomial function of order less than one and greater than zero.

5. The apparatus according to claim 1, wherein the circuitry is further configured to modify the statistical weights by
generating the low-frequency components by low-pass filtering the statistical weights,
generating the high-frequency components by dividing the statistical weights by the low-frequency components, and
operating on the low-frequency components using the first function, which is a compressing function that decreases relative differences between respective values of the low-frequency components.

6. The apparatus according to claim 1, wherein the circuitry is further configured to modify the statistical weights by operating on the high-frequency components to replace each high-frequency component greater than a predetermined threshold by an inverse of the respective high-frequency component.

7. The apparatus according to claim 1, wherein the circuitry is further configured to modify the statistical weights by
using the first function, which is one of a polynomial function and a logarithmic function, and
using the second function, which is one of a polynomial function, a logarithmic function, and an exponential function.

8. The apparatus according to claim 1, wherein the circuitry is further configured to reconstruct the image by minimizing a PWLS objective function, which includes a product of the modified statistical weights and redundancy weights in a data-fidelity term, and the objective function includes a regularization term.

9. The apparatus according to claim 1, wherein the circuitry is further configured to determine the statistical weights using an estimated variance, which is calculated using the respective pixel-intensity values of the projection data and predetermined dark noise values.

10. An apparatus, comprising:
a gantry including a rotating member;
an X-ray source radiating X-rays, the X-ray source fixed to the rotating member;
a plurality of detector elements fixed to the rotating member and arranged diametrically opposed to the X-ray source; and
circuitry configured to
receive the projection data from the plurality of detector elements,
determine statistical weights corresponding to respective pixel-intensity values of the projection data,
modify the statistical weights by generating high-frequency components and low-frequency components of the statistical weights, operating on the low-frequency components using a predefined first function, and operating on the high-frequency components using a predefined second function to generate modified weights, and
reconstruct an image by minimizing an objective function, which includes the modified statistical weights.

11. The apparatus according to claim 10, wherein the circuitry is further configured to modify the statistical weights by operating on the low-frequency components using the first function, which is a compressing function that decreases relative differences between respective values of the statistical weights, wherein the first function is one of a polynomial function and a logarithmic function.

12. The apparatus according to claim 10, wherein the circuitry is further configured to modify the statistical weights by
generating the low-frequency components by low-pass filtering the statistical weights,
generating the high-frequency components by dividing the statistical weights by the low-frequency components, and
operating on the low-frequency components using the first function, which is a compressing function that decreases relative differences between respective values of the low-frequency components.

13. The apparatus according to claim 12, wherein the circuitry is further configured to modify the statistical weights by operating on the high-frequency components to replace each high-frequency component greater than a predetermined threshold by an inverse of the respective high-frequency component.

14. A method, comprising:
obtaining projection data representing an intensity of X-ray radiation detected at a plurality of detector elements;
determining statistical weights corresponding to respective pixel-intensity values of the projection data;
modifying the statistical weights by generating high-frequency components and low-frequency components of the statistical weights, operating on the low-frequency components using a predefined first function, and operating on the high-frequency components using a predefined second function to generate modified weights; and
reconstructing an image by minimizing an objective function, which includes the modified statistical weights.

15. The method according to claim 14, wherein the modifying of the statistical weights further includes operating on the low-frequency components using the first function, which is a compressing function that decreases relative differences between respective values of the statistical weights, the first function is one of a polynomial function and a logarithmic function.

16. The method according to claim 14, wherein the modifying of the statistical weights further includes
generating the low-frequency components by low-pass filtering the statistical weights,
generating the high-frequency components by dividing the statistical weights by the low-frequency components, and
operating on the low-frequency components using the first function, which is a compressing function that decreases relative differences between respective values of the low-frequency components.

17. The method according to claim 16, wherein the modifying of the statistical weights further includes operating on the high-frequency components to replace each high-frequency component greater than a predetermined threshold by an inverse of the respective high-frequency component.

18. The method according to claim 14, wherein reconstructing of the image includes minimizing a PWLS objective function, which includes a product of the modified statistical weights and redundancy weights, and includes a regularization term.

19. The method according to claim 14, wherein the determining of the statistical weights includes using a signal-to noise ratio calculated using the respective pixel-intensity values of the projection data and predetermined dark noise values.

20. A non-transitory computer readable storage medium including executable instruction, wherein the instructions, when executed by circuitry, cause the circuitry to perform steps of the method according to claim 14.

\* \* \* \* \*